US011617846B2

(12) United States Patent
Rapoport et al.

(10) Patent No.: US 11,617,846 B2
(45) Date of Patent: *Apr. 4, 2023

(54) MULTI-NIGHT TITRATION PRESSURE DETERMINATION

(71) Applicants: FISHER & PAYKEL HEALTHCARE LIMITED, Auckland (NZ); NEW YORK UNIVERSITY, New York, NY (US)

(72) Inventors: David M. Rapoport, New York, NY (US); Indu Ayappa, New York, NY (US); Simei Gomes Wysoski, Auckland (NZ); Sujeewa Wannigama, Auckland (NZ); David Robin Whiting, Auckland (NZ)

(73) Assignees: FISHER & PAYKEL HEALTHCARE LIMITED, Auckland (NZ); NEW YORK UNIVERSITY, New York, NY (US)

( * ) Notice: Subject to any disclaimer, the term of this patent is extended or adjusted under 35 U.S.C. 154(b) by 372 days.

This patent is subject to a terminal disclaimer.

(21) Appl. No.: 16/851,045

(22) Filed: Apr. 16, 2020

(65) Prior Publication Data

US 2020/0238028 A1  Jul. 30, 2020

Related U.S. Application Data

(63) Continuation of application No. 16/420,546, filed on May 23, 2019, now Pat. No. 10,625,036, which is a
(Continued)

(51) Int. Cl.
*A61M 16/00* (2006.01)
*A61M 16/06* (2006.01)
(Continued)

(52) U.S. Cl.
CPC ....... *A61M 16/0069* (2014.02); *A61B 5/4818* (2013.01); *A61M 16/0051* (2013.01);
(Continued)

(58) Field of Classification Search
CPC ............ A61M 16/0069; A61M 16/026; A61M 16/0051; A61M 16/06; A61M 16/08;
(Continued)

(56) References Cited

U.S. PATENT DOCUMENTS 10,322,251 B2 * 6/2019 Rapoport .............. A61M 16/06
10,625,036 B2 * 4/2020 Rapoport ............. A61B 5/4818

\* cited by examiner

*Primary Examiner* — Steven O Douglas
(74) *Attorney, Agent, or Firm* — Fay Kaplun & Marcin, LLP (57) ABSTRACT

A multi-night titration (MNT) process to find an optimal single therapeutic pressure of a CPAP device. This single therapeutic pressure can then be used on an on-going basis by the patient after the titration period. The MNT process differs from current auto adjusting processes used for titration (or ongoing use) in that the MNT process does not respond locally by adjusting pressures to individual events. With existing devices, the continuous adjustment of supplied air pressure always responds to one or a small number of events and thus fails to compensate for a patient's adaptation thereto, resulting in the supply of a less than optimal therapeutic pressure to the patient. While auto adjusting processes often capture and respond well to short-term and transient conditions, the MNT process of the current disclosure seeks to capture long term trends and find the most suitable average single pressure for a patient.

20 Claims, 11 Drawing Sheets

Related U.S. Application Data continuation of application No. 14/775,994, filed as application No. PCT/US2014/022633 on Mar. 10, 2014, now Pat. No. 10,322,251.

(60) Provisional application No. 61/793,070, filed on Mar. 15, 2013.

(51) Int. Cl.
  *A61B 5/00* (2006.01)
  *A61M 16/08* (2006.01)
  *A61B 5/087* (2006.01)

(52) U.S. Cl.
  CPC .......... *A61M 16/026* (2017.08); *A61M 16/06* (2013.01); *A61M 16/08* (2013.01); *A61B 5/087* (2013.01); *A61M 2016/0027* (2013.01); *A61M 2016/0033* (2013.01); *A61M 2205/3303* (2013.01); *A61M 2205/3331* (2013.01); *A61M 2205/3355* (2013.01); *A61M 2205/52* (2013.01); *A61M 2230/46* (2013.01)

(58) Field of Classification Search
  CPC .. A61M 2016/0027; A61M 2016/0033; A61M 2205/3303; A61M 2205/3331; A61M 2205/3355; A61M 2205/52; A61M 2230/46; A61B 5/4818; A61B 5/087
  See application file for complete search history.

MULTI-NIGHT TITRATION PRESSURE DETERMINATION

CROSS-REFERENCE TO RELATED APPLICATIONS

This application is a Continuation of U.S. patent application Ser. No. 16/420,546 filed on May 23, 2019, now U.S. Pat. No. 10,625,036; which is Continuation of U.S. patent application Ser. No. 14/775,994 filed on Sep. 14, 2015, now U.S. Pat. No. 10,322,251; which is a National Phase application of PCT Application Serial No. PCT/US2014/022633 filed on Mar. 10, 2014; which claims priority to U.S. Provisional Application Ser. No. 61/793,070 filed on Mar. 15, 2013. Specifications of the above patent(s)/application(s) are expressly incorporated herein, in their entirety, by reference.

PARTIES OF JOINT RESEARCH AGREEMENT

The present disclosure was made as a result of activities undertaken within the scope of a written joint research agreement between Fisher & Paykel Healthcare Limited and New York University.

FIELD

The present disclosure relates to the field of continuous positive airway pressure (CPAP) titrating devices.

BACKGROUND

Patients suffering from breathing disorders, including for example, sleep disordered breathing (SDB) and obstructive sleep apnea (OSA), are often advised to use a continuous positive airway pressure (CPAP) device. CPAP devices use positive air pressure to keep the patients airways from collapsing as they breathe. There are two main types of CPAP devices. These include single or bi-level pressure CPAP devices that maintain a given pressure or set of pressures and auto titrating CPAP devices which rapidly change pressures in response to breathing events.

When a patient first obtains a CPAP device, it is common for them to visit a sleep clinic in order to determine appropriate pressure settings for their CPAP device. This is particularly true for single pressure or bi-level pressure CPAP devices, but can also include auto titrating devices. Sleep clinic evaluations can be costly and often require an overnight stay at the sleep clinic. Moreover, patients often visit a sleep clinic for a very short period of time, such as a single night, resulting in only limited information about the patient. Even after a sleep clinic visit, patient's often experience discomfort if the selected pressure for the CPAP device is not optimal. This necessitates a costly return visit to a sleep clinic.

Auto-titrating CPAP devices attempt to alleviate this problem by monitoring breathing patterns of a patient and then rapidly and automatically adjusting a pressure supplied to the patient based on the occurrence of any abnormal breathing events, without waiting to see if the events recur at that pressure. However, patients often do not tolerate the use of continuously adapting pressures over extended periods of time or prefer a single pressure once that single pressure is titrated optimally.

SUMMARY

The present disclosure provides a multi-night titration (MNT) process to find an optimal single therapeutic pressure of a CPAP device. This single therapeutic pressure can then be used on an on-going basis by the patient after the titration period. The MNT process differs from current auto adjusting processes used for titration (or ongoing use) in that the MNT process does not respond locally by adjusting pressures to individual events. With existing devices, the continuous adjustment of supplied air pressure always responds to one or a small number of events and thus fails to compensate for a patient's adaptation thereto, resulting in the supply of a less than optimal therapeutic pressure to the patient. While auto adjusting processes often capture and respond well to short-term and transient conditions, the MNT process of the current disclosure seeks to capture long term trends and find the most suitable average single pressure for a patient.

The MNT process disclosed herein uses data collected at different pressures over several sessions or several nights to find an optimal therapeutic pressure by capturing short and long term trends and the effects thereof. Embodiments of the MNT process according to the disclosure seek to capture long term trends and find the most suitable average single pressure for a patient, taking into consideration changes the patient may experience over time including position, sleep state, alcohol use etc. During the normal course of titration, the MNT process does not respond to individual respiratory events such as, for example, single apneas, hypopneas and short periods of inspiratory flow limitation. The MNT process is adapted to automatically collect and analyze patient data at sub-therapeutic, therapeutic and above-therapeutic pressures to subsequently estimate the best therapeutic pressure and accurately assess its overall effectiveness over sustained periods. As will be described in greater detail herein, the MNT process can be composed of either one or two steps.

DETAILED DESCRIPTION

Figure 1:
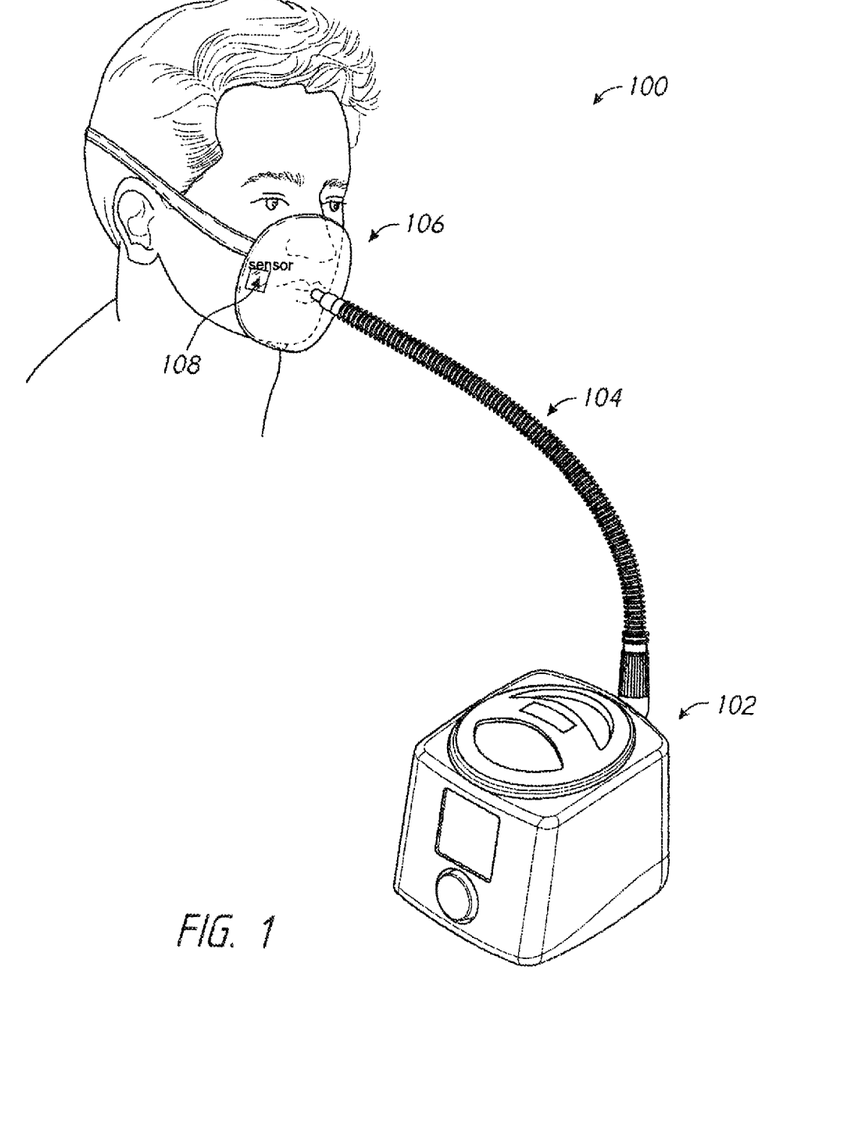
FIG. 1 depicts an embodiment of a CPAP system.

FIG. 1 illustrates an embodiment of a CPAP system 100 according to the present disclosure. The system includes a CPAP device 102, a tube 104 and a mask 106. The mask 106, in use, is positioned over one or both of a nose and face of the patient to supply a positive air pressure thereto. In an embodiment, the CPAP system 100 also includes a sensor 108 positioned in one or both of the mask 106 and tube 104 in order to monitor air flow there through. In an embodiment, the sensor is a flow sensor placed in the system before the blower. In an embodiment, the sensor is a pressure sensor placed in the system after the blower, but before the humidifier. As will be understood by those of skill in the art, the sensor can be any of a number of sensors located at various locations in the system that are capable of detecting operating characteristics of the system and flow states of the patient.

Figure 2:
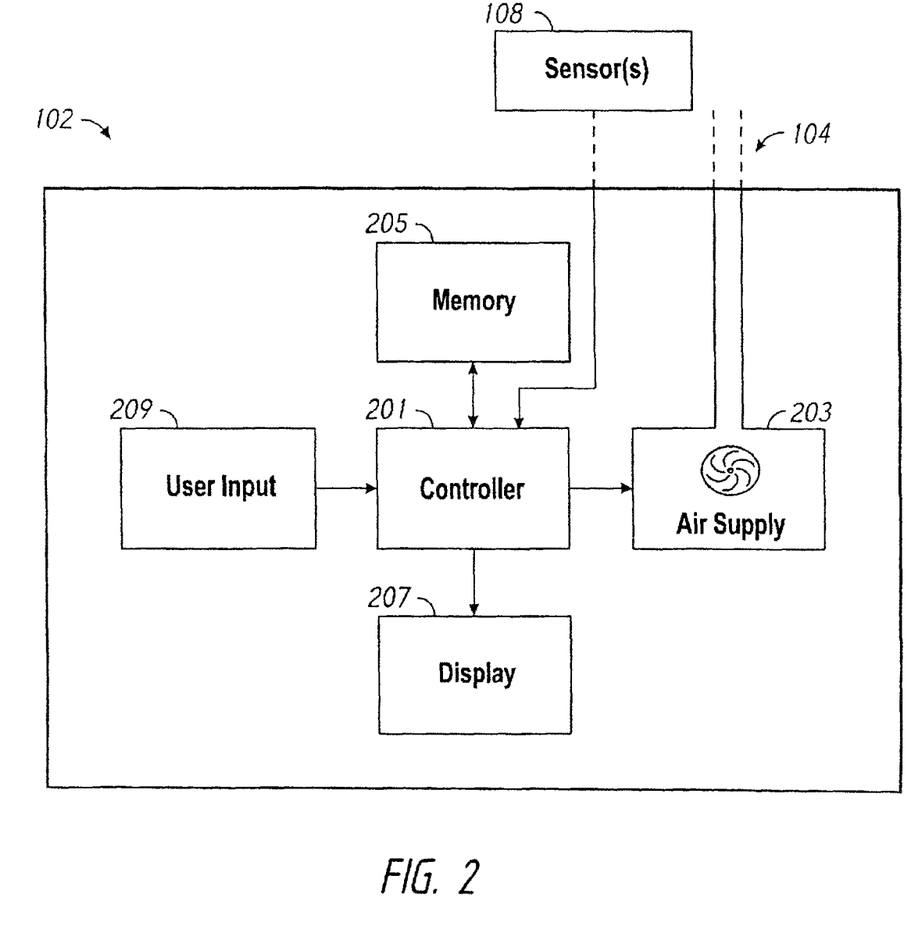
FIG. 2 illustrates a schematic diagram of a CPAP device.

FIG. 2 illustrates a schematic depiction of CPAP device 102. CPAP device 102 includes a controller 201, an air supply 203, a memory device 205, and optionally a display 207 and user inputs 209. The controller 201 controls the operation of the CPAP device 102. The controller 201 can include, for example, analog or digital processors or other electronic control devices as would be understood by a person of skill in the art from the present disclosure. The controller 201 controls the operation of the air supply 203. The controller also receives and analyzes sensor signals from sensor(s) 108. The controller 201 communicates with the memory device 205 to store information including operating information, sensor information, and other information as would be understood by a person of skill in the art and as disclosed herein. The controller can also optionally receive commands from a user input 209 as well as communicate output information to the display 207.

Figure 3:
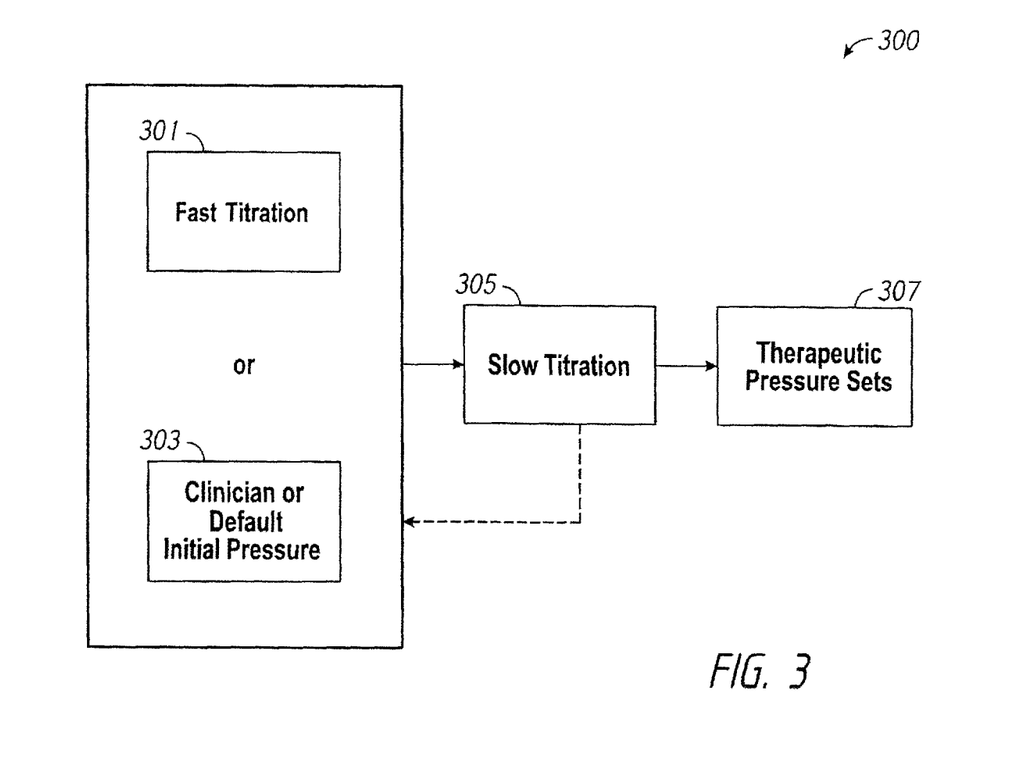
FIG. 3 depicts a flow chart of an MNT process.

FIG. 3 illustrates an embodiment of a MNT process 300 according to the present disclosure. The MNT process 300 can either begin with an optional fast titration process 301 or an initial clinician set or default pressure 303. The fast titration process 301 is carried out to quickly determine, based on short term events, an initial therapeutic pressure close to optimal therapeutic levels. The optional fast titration process 301 avoids the need for the patient to experience pressures significantly different from the optimal therapeutic level for long periods of time, thereby reducing discomfort.

Once an initial pressure is determined, either by the fast titration process 301 or through a clinician/default set value 303, the MNT process 300 proceeds to a slow titration process 305. The slow titration process 305 determines secondary therapeutic pressure based on information from multiple sessions (each potentially several hours long). These sessions operate at pressures (1) below the initial therapeutic pressure, (2) at the initial therapeutic pressure and (3) above the initial therapeutic pressure. The information from these sessions is then stored in a storage device, such as memory device 205, and further integrated into a single secondary prescription pressure for ongoing treatment by a processing arrangement, such as, for example, controller 201.

Figure 3A:
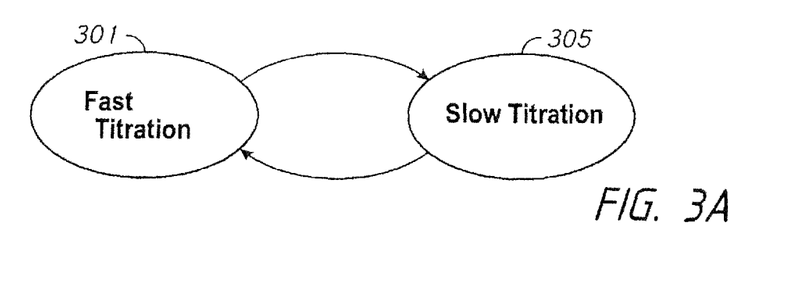
FIG. 3A depicts a flow chart illustrating an interaction between a fast titration system and a slow titration system.

In an embodiment, the fast titration process 301 and slow titration process 305 may operate either sequentially or in parallel, depending on the configuration and can occur recursively if periods of severely elevated sleep disordered breathing are unexpectedly detected during the slow titration process 305. This type of recursive system is illustrated in FIG. 3A. In another embodiment, the slow titration process 305 may be employed independently of the fast titration process 301 as the sole MNT titration process.

Embodiments of the MNT processes, including the fast titration and slow titration processes, disclosed herein are based on one or several indices of sleep disordered breathing (SDB). These indices indicate the frequency and/or severity of the sleep disordered breathing over the collection interval and are used to determine future pressure adjustments.

In the fast titration process, the collection intervals are relatively short and intended to move a patient quickly to an acceptable pressure to begin the slow titration process.

In the slow titration process, the collection intervals are chosen to be long enough to be representative of the individual's long term behavior. This avoids the pitfalls of quickly adjusting pressure at the occurrence of small clusters of events as is typically done by conventional autotitrating CPAP processes.

Examples of appropriate SDB indices include, but are not limited to, apnea-hypopnea index (AHI), respiratory disturbance index (RDI), percent sustained flow limitation (% SFL), and one or more obstruction indices (OI).

AHI captures the rate of occurrence of typical apneas and hypopneas as an Index over time (events/hour).

RDI captures the rate of occurrence of apneas, hypopneas, and more subtle events like respiratory-effort related arousals (RERA's) as an index over time.

% SFL corresponds to a percentage of time spent or percentage of breaths where there is evidence of elevated upper airway resistance or collapsibility (i.e., sustained flow limitation evidenced by the shape of the inspiratory airflow contour).

One or more OIs are usually mathematical combinations of the AHI and % SFL (for example AHI+⅓*% SFL).

Other useful information which can also be captured and used in the MNT process can include awake time, sleep state and leakage.

While the simplest process for determining an optimal MNT pressure ($P_{MNT}$), each time the MNT process is performed, it uses only a single one of the above SDB indices, it is also possible to combine or use different SDB indices for different parts of the process or a combination of indices for every or various parts of the process. For example, the fast titration process may titrate on AHI, whereas the slow titration process may titrate on OI. Thus, it is noted that the present disclosure covers any combination of SDB indices with any of the disclosed processes. Furthermore, during the operation of the slow titration process acting on one index (for example the OI), a concurrent monitoring of another index (such as the AHI, which typically measures the more severe breathing events) can be used to modify or abort the slow titration process when this second sleep disordered breathing index rises above a predetermined limit for at least a predetermined time period. The predetermined limit can be, for example, a limit indicative of severe impairment. The predetermined time period can be, for example, one hour.

Figure 4:
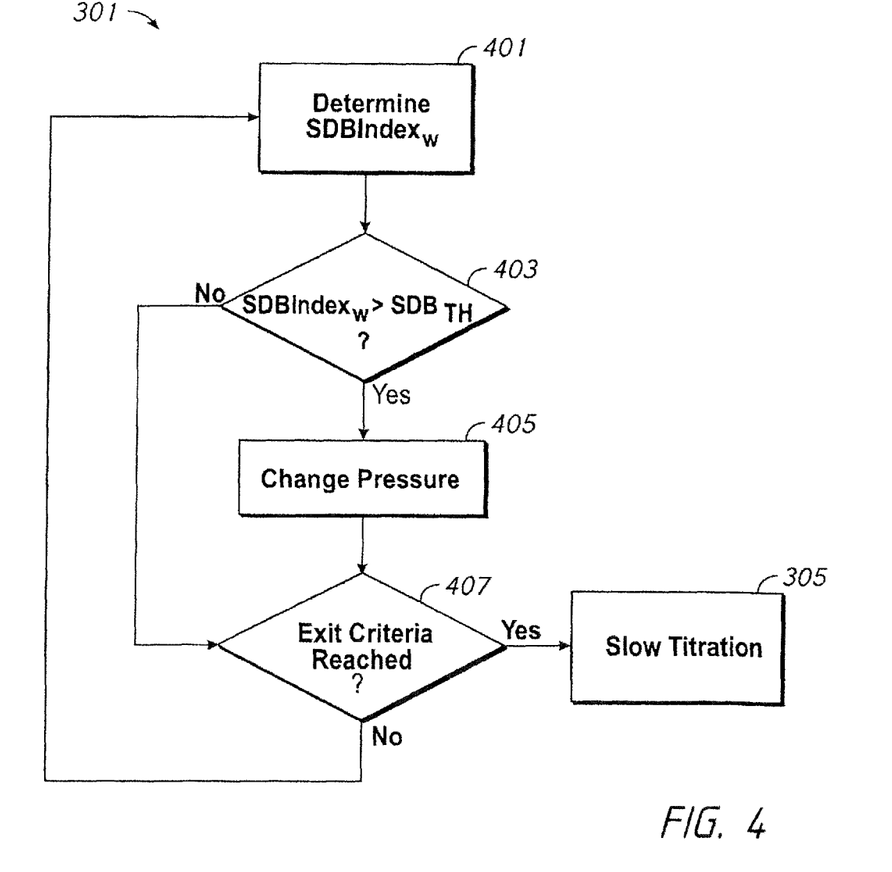
FIG. 4 depicts an embodiment of a fast titration process.

An embodiment of the fast titration process 301 is described in greater detail with respect to FIG. 4. The fast titration process responds to small numbers of individual events or to relatively short periods of data collection (such as, for example, 1 hour) and integrates multiple events into a sleep disordered breathing index (such as, for example, an OI). The fast titration process responds to severe sleep disordered breathing as this occurs by raising CPAP pressure. The goal is to raise the pressure into a range that reduces severity of the sleep disordered breathing from severe to mild-moderate, as those skilled in the art will understand. The fast titration processes can be implemented by analyzing one or several SDB indices ($SDBIndex_w$). As described above, these indices are analyzed over a relatively short time window w and the fast titration process changes the pressure repeatedly based on these relatively short durations. Specifically, referring to FIG. 4, starting at step 401, the system determines an $SDBIndex_w$ over a given time window. Once the index is determined, the system moves to step 403 where the system determines whether an $SDBIndex_w$ at the current index pressure is greater than the targeted partially therapeutic SDB index $SDB_{Th}$. If $SDBIndex_w$ is greater (i.e., the pressure is still sub-therapeutic), the method proceeds to step 405 where the supplied pressure is increased (or decreased) by a value ΔP. The system then moves to step 407 where fast titration exit criteria is analyzed to determine if an appropriate pressure has been reached to begin the slow titration process. If the exit criteria has not been reached at step 407, the system returns to step 401 where the $SDBIndex_w$ is re-determined at the new pressure over a new time window. If it is determined in step 403 that $SDBIndex_w$ is not greater than $SDB_{Th}$, the process can skip step 405 and proceed directly to step 407.

The process continues to loop until at least one exit criteria is reached. The fast titration process continues to adjust the supplied air pressure until an exit criterion is reached in step 407. In such a case, the fast titration process passes control to the slow titration process 305. The slow titration process determines a secondary therapeutic pressure, as described in greater detail herein.

The exit criteria of step 407 may correspond to a condition where the process does not detect a need for further pressure changes. For example, the exit criteria can be that no net change in pressure occurs for a predetermined period of time (e.g., about 3 hours, an entire night, etc.). In an embodiment, this can be longer than the length of one individual data collection period. The exit criteria may also correspond to a condition wherein the process changes the pressure both up and down, but the supplied pressure remains below a determined pressure for a specified fraction of the time (e.g., 80-90% of total titration time). In such a situation, the supplied pressure or a pressure slightly below the supplied pressure is chosen as the start of the slow titration process 305.

The fast titration process 301 of FIG. 4 is configured to select a pressure that treats the majority of the sleep disordered breathing by a first relatively crude criterion. This results in a selection of an initial therapeutic pressure within a predetermined acceptable range of a final ideal therapeutic pressure. This range is intended to at least partially treat the patient by reducing the severity of sleep disordered breathing events. In an embodiment, the initial therapeutic pressure is chosen to be predictably below or near the final ideal therapeutic pressure. The initial therapeutic pressure is then refined by the slow titration process 305, which is described in greater detail hereinafter with respect to FIG. 5.

In an embodiment, the fast titration process is performed by an auto-adjusting or auto-titration device (collectively referred to herein as an auto CPAP device). In an embodiment an auto CPAP device is used for a certain period of time by the patient, for example, a predetermined number of days. In an embodiment, the initial pressure supplied to the slow titration process is based on the operation of the auto CPAP device. For example, in an embodiment, the $90^{th}$ percentile (or other percentile) pressure used by the CPAP device is determined and used as the initial pressure for the slow titration process. In an embodiment, a simple average CPAP pressure can be used as the initial pressure for the slow titration process. Other methods can be employed to determine the initial pressure based on the auto CPAP device's supplied pressure.

Figure 5:
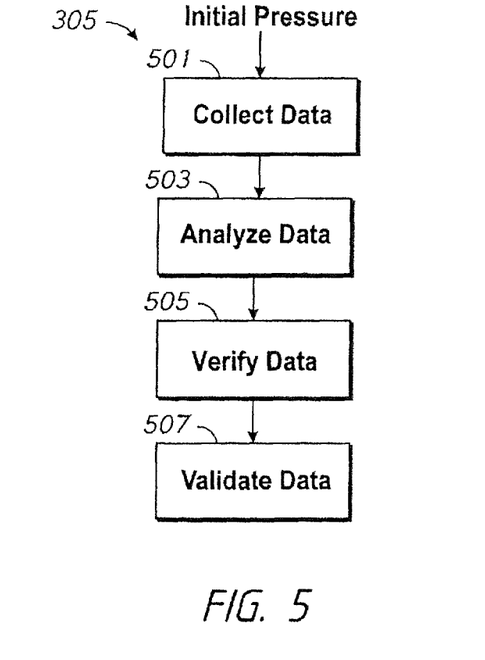
FIG. 5 depicts an embodiment of a slow titration process.

The slow titration process 305 is configured to refine, during its performance, the initial therapeutic pressure that has already been supplied with the intent of determining a therapeutic pressure ($P_{MNT}$) that is optimized for use in a sustained single CPAP prescription.

The main process for determination of $P_{MNT}$ via the slow titration process 305 is composed of four main parts that can be used as a single pass or applied recursively. The slow titration process 305 includes the steps of data collection to the point of having sufficient data over multiple pressures (step 501), data analysis to determine the optimal pressure for prescription (step 503), verification of quality of result (i.e., an efficacy of the prescribed pressure) (step 505) and validation of effectiveness over additional time periods (step 507), as will be described in greater detail below.

The data collection of step 501 occurs over multiple intervals of time. Each interval of time is designed to capture the entire expression of sleep disordered breathing over more than one state rather than instantaneously. In other words, each interval is designed with sufficient time to gain a picture of the average value of OI over a full sleep cycle and/or during multiple positions. As such, the data collection periods are generally longer for each data point than in the fast titration process 301. The intervals can range from several hours to a full day.

In an embodiment, the interval is in a range between about 1-2 hours and about 8 hours or one full night. In an embodiment, the interval is about 3 hours. In an embodiment, the range is greater than about 3 hours. In an embodiment, the interval varies so that a predetermined minimum of acceptable data is obtained for each interval. For example, if about 3 hours of data is desired, it may take about 5 hours at a single pressure to obtain about 3 acceptable hours of data because about 2 hours may be corrupted by the patient waking up or the detection of air leakage at an unacceptable rate. Moreover, if an interval is interrupted, for example, by the patient discontinuing use of the machine, the interval can be restarted or simply continued when the patient returns to use of the machine. In an embodiment, data can also be collected in a manner designed to anticipate a minimal value that would occur if the period were extended. For example, an OI of 45 in one hour anticipates a minimal OI value of 15 in about 3 hours. Thus, the process may be configured to abort a data collection period and extrapolate the result based on anticipatory results.

Any one or several determined SDB indices, $SDBIndex_w$, may be collected over at least several time windows and should include at least some data collections at a range of pressures. For example, the range of pressures can include a combination of pressures that are below the initial therapeutic pressure, at the initial therapeutic pressure and above the initial therapeutic pressure levels. This range of data collection is chosen to include the pressure achieved by the fast titration process 301 if performed. Alternatively, the slow titration may start at a predetermined level (e.g., 0 cm $H_2O$, 4 cm $H_2O$ or a prescribed value) or clinician set level, if no fast titration has been performed. The range of pressures used to collect multiple data windows may then be modified to guarantee that the process collects data at least at one pressure that is sub-therapeutic (below the initial therapeutic pressure) and one that reaches into the therapeutic range (at pressures at least as great as the initial therapeutic pressure).

Of course other combinations of pressures can also be chosen. Moreover, multiple sessions can be performed at different time periods using the same pressure interspersed with other pressures. For example, the system can start with a therapeutic pressure and move to a sub-therapeutic pressure and then return to a therapeutic pressure before moving to an above therapeutic level.

In its simplest form, data collection is performed by collecting the SDB indices several times (for example, 3 times for about 3 hours at a single pressure) for each of multiple pressures over a range of pressures including and extending on either side of the initial preliminary therapeutic pressure. Each data collection period lasts for a pre-defined time and results in a calculation of each relevant $SDBIndex_w$. This collection of relevant $SDBIndex_w$s can then be averaged for all time periods collected at that pressure or used as individual data points in the data analysis. In an embodiment, the pressure levels and time periods are pre-defined relative to the initial pressure. The data for each collection period is not analyzed until all data from each pressure range is collected for the appropriate amount of time. In an embodiment, of such a collection system, escape criteria based on a high SDB index value can be used to abort collection at a particular pressure level.

In an embodiment, pressure levels can increase sequentially from a sub-therapeutic level to an above therapeutic level. In such an embodiment, a first low pressure can be chosen relative to an initial pressure. Once collection at the first pressure is completed, the system will increase the pressure by a predetermined amount. For example, this pressure increase can be 1 cm $H_2O$. In other embodiments, the pressure increase can be 0.5 cm $H_2O$ or in a range between 0.1 cm $H_2O$ to 2 cm $H_2O$. The data collection then continues to step through all desired pressure levels sequentially until all data is collected at the predetermined pressure levels for the predetermined period of time. The system can them move to the data analysis step 503 to analyze the data. In an embodiment, the data analysis step 503 can also determine if sufficient acceptable data has been collected and can return the titration process back to step 501 if needed to collect additional data.

Alternatively, the slow titration process 305 can collect data from an initial set of pressure levels and extend this pressure range based on the results obtained. An example of this is described below in detail hereinafter. Specifically, in step 501, the initial data is collected at pressures referenced relative to the starting pressure P (such as, for example, P−1, P, P+1, P+2, P+3). The SDB indices obtained from these collection periods are then examined. If the SDBIndex for the lower pressure(s) is not above the therapeutic value (such as, for example, the lowest pressure collected so far is not sub-therapeutic), further data points are collected at one or both of the lowest pressure(s) and a lower pressure until a sub-therapeutic condition is reached. The lowest SDBIndex from the initial collection periods is also examined, and typically occurs at the highest pressure P. If the SDB indices for the higher pressure(s) is not below the therapeutic value (such as, for example, the highest pressure collected until this point is not yet high enough to be classified as therapeutic), further data points are collected at the highest and/or higher pressures until an optimal therapeutic condition is reached as judged from the SDB index. In an embodiment, if the SDBIndex for a certain pressure is higher than a threshold (such as, for example, 10), the process can increase the pressure by a higher change in pressure than would otherwise occur (such as, for example, jumping from a pressure of 5 cm $H_2O$ to 6 or 7 cm $H_2O$ instead of a normal jump to 5 cm $H_2O$).

The clock recording elapsed duration of a window may be stopped when a session of data (such as, for example about 3 hours of data at one pressure in an embodiment) is interrupted. The interruption can be, for example, the end of the night, when it is determined that the patient has awoken, when there is a high leakage rate, or when the patient removes the mask. Alternatively, the total targeted duration of one data collection window may be adjusted such that it is terminated anytime the flow becomes invalid or the machine is turned off, provided it is greater than some minimum threshold (such as, for example, about 2 hours in an embodiment) but otherwise continue to the target window length. If the collected data is less than the lower threshold, that window continues to accrue on the next time or night when the same pressure is delivered. In an embodiment, data is collected until a sufficient amount of both sub-therapeutic and therapeutic pressures are collected as judged by the SDB index.

Figure 5A:
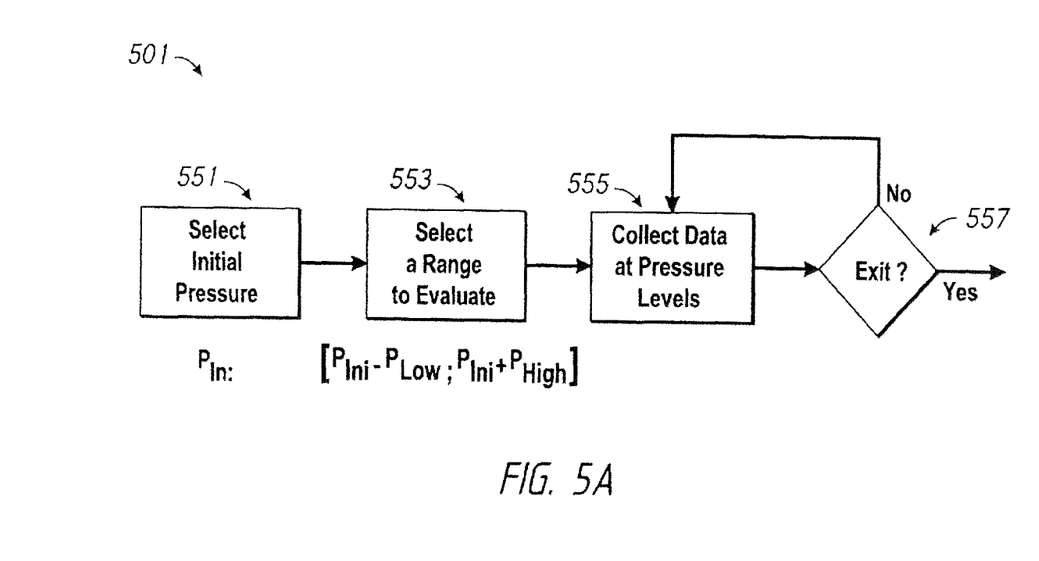
FIG. 5A depicts further details of an embodiment of a slow titration process.

FIG. 5A illustrates one potential embodiment of the data collection step 501. The process can start with an initial pressure ($P_{Ini}$) as described above. The process then moves to step 553 where a range of pressures to be evaluated are selected. For example, this can be a range including predetermined pressure offsets from the initial pressure, such as, for example, $P_{Ini}-P_{low}$; $P_{Ini}+P_{high}$, etc. The process then moves to step 555 where pressure level data is collected. At step 557, the collected pressure level data is initially analyzed to determine if the data collection process 501 should be exited. The exit criteria can include, for example, a determination that all desired levels of pressure have been evaluated or that an optimal pressure has been determined.

When sufficient data has been collected, data collection at further pressures is ended and the method proceeds to step 503, where the collected data is analyzed to choose an optimal pressure $P_{MNT}$. In an embodiment, the analysis can be performed on all the data collected in the multiple intervals and at the multiple pressures. In other embodiments, the data is passed through an initial screening to confirm that it represents acceptable measurements. For example, this can include determining if the collected data was corrupted by the patient's wakefulness during an individual session or if the leakage rate was too high during the session. Alternatively, this initial screening can be performed at the data collection step 501 in order to ensure that sufficient acceptable data is collected at each pressure.

Figure 6:
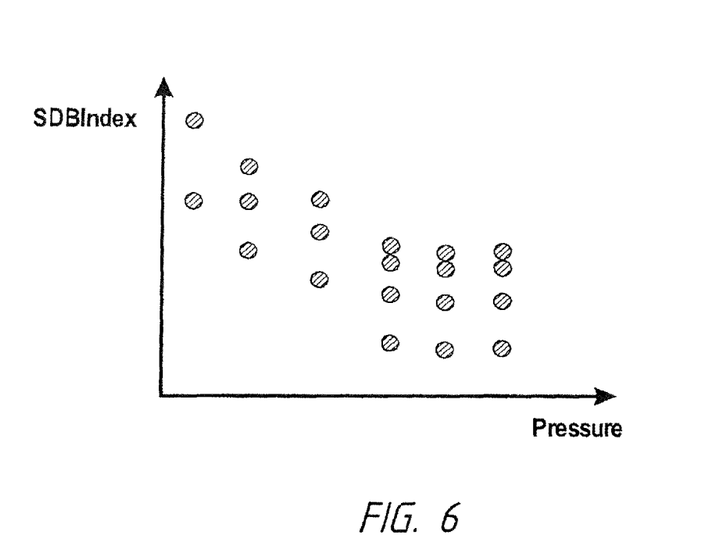
FIG. 6 depicts a plot of a sleep disordered breathing index versus pressure.

Once a set of data is established for analysis, one or more of several mathematical approaches is used to determine the best pressure $P_{MNT}$ for continuous CPAP that will be prescribed after the MNT titration. One approach to finding the best pressure is to examine the characteristics of the $SDBIndex_w$ vs. Pressure graph, as shown in FIG. 6. The determination of the optimal (or therapeutic) pressure $P_{MNT}$ can be made using a process that is based on one or more characteristics of the plot of FIG. 6 as will be described in greater detail hereinafter. Each graphed point on the plot of FIG. 6 represents the $SDBIndex_w$ determined for a given pressure during a data collection interval. In the graph of FIG. 6, for example, three intervals of data were collected from each pressure and an SDBIndex value was determined from each interval at each pressure and plotted on the graph. Of course it is to be understood that the calculation can also be performed using an average value for each pressure determined from multiple sessions collected at that pressure.

In an alternative embodiment, the data analysis step 503 may be carried out in two phases: a first phase including the use of the characteristics of the curve to pick a first estimate of the $P_{MNT}$ and a second phase including refining this estimate using additional characteristics of the curve described in greater detail below. Although shown in graphical form in the drawings, it is to be understood that actual graphs may not be determined as part of the data analysis step 503. Rather, a series of mathematical equations is performed to generate an output pressure indication using the concepts described herein. Of course, it is to be understood that the set of data can also be downloaded and/or displayed as a graph for manual review and evaluation.

In an embodiment, as discussed above, calculations of SDBIndex for use in the data collection and analysis portions of the slow titration process 305 are made at a single pressure. During the collection period for each pressure there may be external factors that lead to pressure changes. These periods of pressure deviation can be excluded from the analysis, as is their contribution to elapsed time of the window. The exclusion can result in a shortened window of a collection period or it can result in entire collection periods being excluded. Events leading to exclusion can include, but are not limited to: periods of high leak leading to a drop in pressure or deterioration of the flow signal, periods of intentional pressure reduction such as triggered by Sens-Awake (or other patient awake technology that lowers a pressure when it is detected that a patient is awake) or other comfort technologies intended to drop therapeutic pressure during periods of arousal (this would not apply to pressure drops with a single breath such as with Respironic's C-flex™), and periods during a ramp at the beginning of a recording session that might particularly occur during the data collection periods. As those skilled in the art will understand, these periods may also occur when the patient first turns on the CPAP machine if it is set to be used at a low pressure until a sleep onset event occurs.

Figure 7:
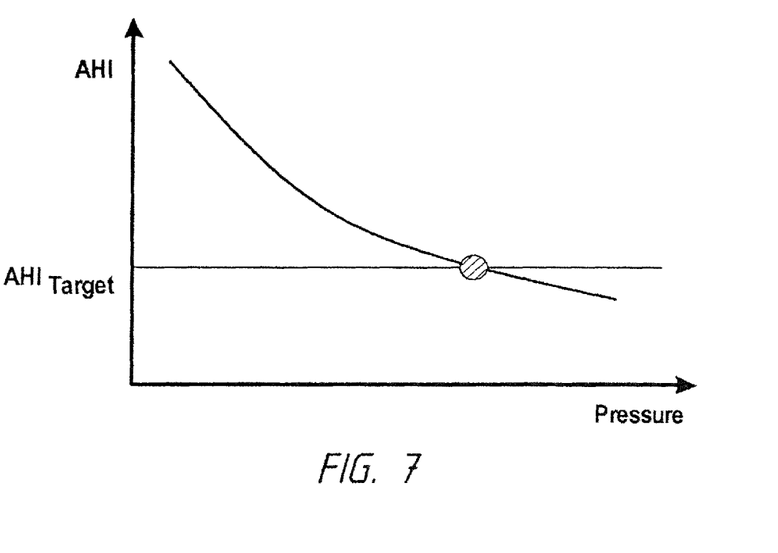
FIG. 7 depicts an optimal pressure of the plot of FIG. 6, calculated via a target crossing calculation.

FIGS. 7-10 depict examples of some specific calculated characteristics of the collected data according to the disclosure. FIG. 7 is directed to a target crossing process for calculating an optimal pressure. In this embodiment, the therapeutic pressure $P_{MNT}$ is determined by finding the point where an extrapolated or fitted curve of the data collection for the SDBIndex crosses a certain target level, SDBIndex$_{Target}$. This target level is considered to be the therapeutic level. FIG. 7 illustrates an embodiment where the SDBIndex$_{Target}$ is an AHI level, AHI$_{Target}$, and the therapeutic pressure is the pressure at the point where the AHI level crosses the AHI$_{Target}$. For example, this target level can be an AHI of 5. In other embodiments, other SDB indicia can be used. This can include for example, an OI level or other SDB indicia as would be understood by a person of skill in the art. In an embodiment, the OI$_{Target}$ threshold can be 10.

Figure 8:
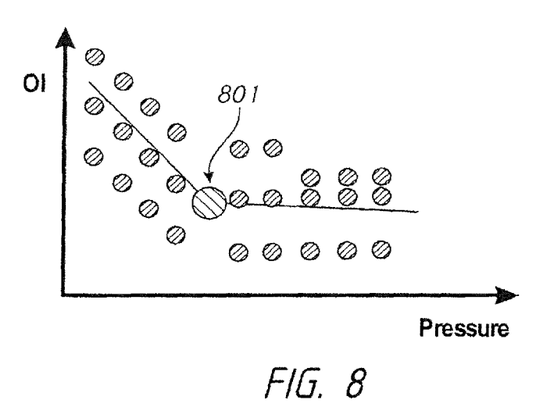
FIG. 8 depicts an optimal pressure of the plot of FIG. 6, calculated via determination of an inflection point.

FIG. 8 is directed to an inflection point calculation. The inflection point is determined from a comparison of SDBIndex$_w$ vs. Pressure similar to FIG. 6. As those skilled in the art will understand, such a determination is useful when the SDB indices do not have a simple linear relationship with the pressure changes and the SDBindex$_w$ vs. Pressure indicate a clear point at which further changes in pressure either produce no further improvement or a different (typically flatter) response with further increases in pressure. One technique for determining this point is to use a piece-wise linear regression. The decision that this has been successfully applied can be based on the strength of the regression coefficient $r^2$. In FIG. 8, the SDBIndex$_w$ are OI values and a clear inflection point 801 is illustrated.

Figure 9:
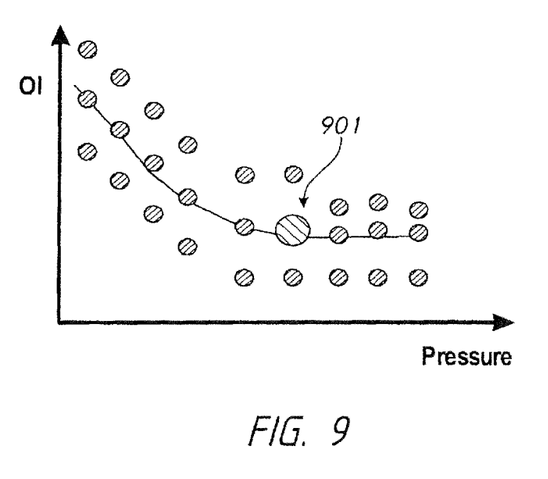
FIG. 9 depicts the selection of an optimal pressure of the plot of FIG. 6, calculated via determination of slope change.

FIG. 9 is directed to a Slope Change calculation. The Slope Change calculation is an evaluation of a pressure via a determination of a slope change in the plot of SDBIndex$_w$ vs. Pressure similar to FIG. 6. The Slope Change calculation may be especially useful when the plot of FIG. 6 follows a curvilinear relationship and no simple inflection point is found. Specifically, the curve fitted to the data of SDBIndex$_w$ vs. Pressure may show a curvilinear relationship such that, above a certain pressure, the negative slope is so small that regardless of pressure increase, the SDB index does not change significantly. In FIG. 9, the SDBIndex$_w$ are OI values and the pressure at point 901 is chosen because above that pressure, the negative slope is so small that SDB index does not change significantly with pressure increases.

Figure 10:
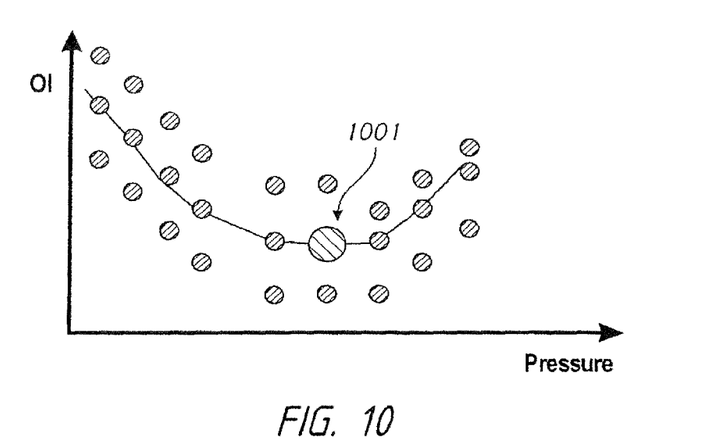
FIG. 10 depicts an optimal pressure of the plot of FIG. 6, calculated via determination of a minimum sleep disordered breathing index point.

FIG. 10 is directed to an SDB Index Peak calculation determination. This calculation compares SDBIndex$_w$ vs. Pressure (again, similar to FIG. 6) to determine a pressure at which SDBIndex$_w$ assumes its overall minimum or maximum value, irrespective of target, slope or inflection of the curve. In FIG. 10, for example, the peak minimum pressure is shown at point 1001.

Once the characteristics of the curve have been analyzed according to any or a combination of the techniques disclosed above, the characteristics can be incorporated into a process to find the optimal pressure $P_{MNT}$. As an example of one such process, a selection of one of the characteristics above is made to find a first approximation of $P_{MNT}$, then, in a second pass, examination the characteristics of the entire dataset in the vicinity (up or down) from that pressure is performed to refine the choice.

Figure 11:
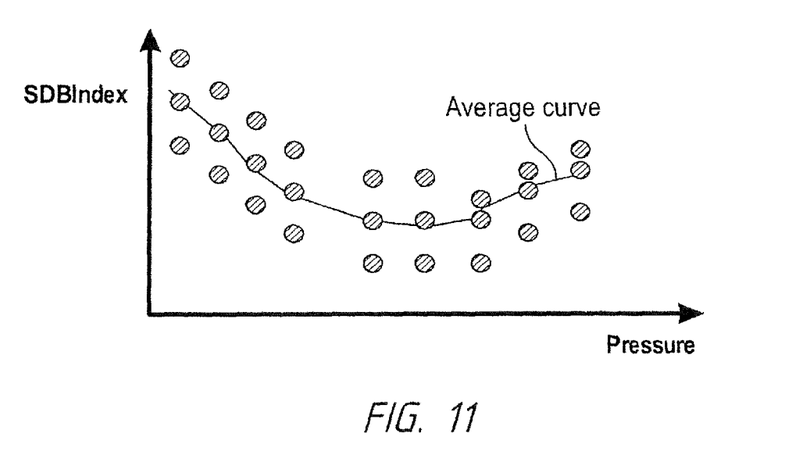
FIG. 11 depicts determination of an average curve from the data in the plot in FIG. 6.
Figure 12:
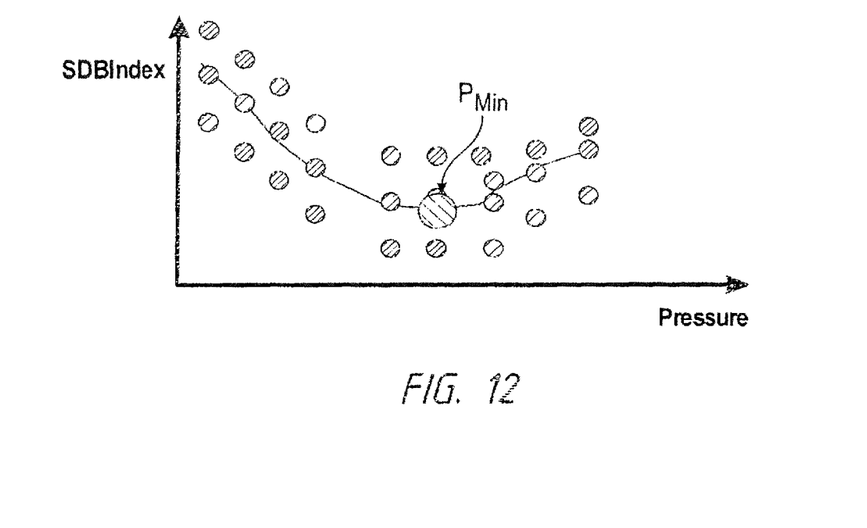
FIG. 12 depicts the determination of a minimum sleep disordered breathing index point using the average curve generated in FIG. 11.
Figure 13:
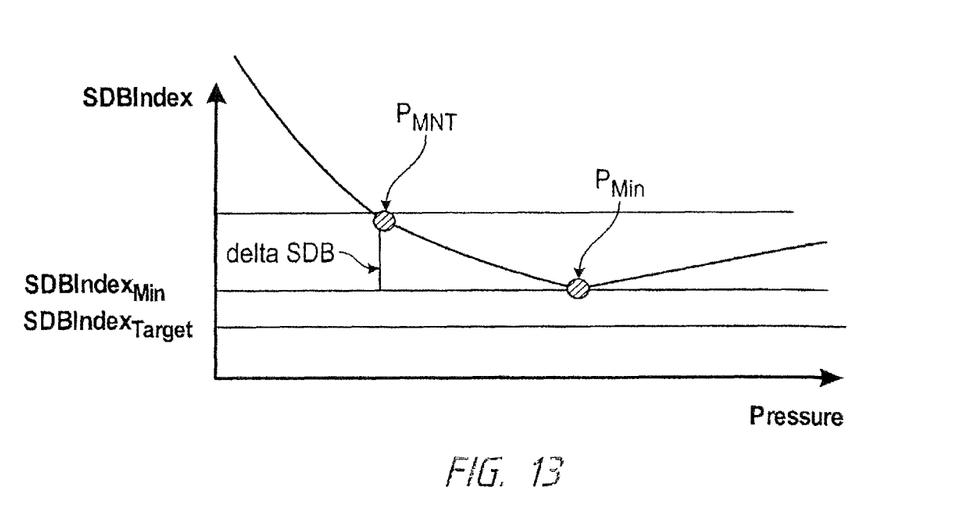
FIG. 13 depicts the selection of an optimal pressure at a pressure below a minimum pressure at a point after which a sleep disordered breathing index does not improve significantly upon pressure increase.

In one embodiment of the slow titration process, as shown in FIG. 11, collected data at each pressure for the pressure range may be averaged to display an average curve. From this average curve, a first approximation of $P_{MNT}$ may be determined by selecting the pressure $P_{Min}$ associated with a lowest value of the SDBIndex, SDBIndex$_{Min}$, as shown in FIG. 12. In a next step, the data analysis is continued from $P_{Min}$ and includes only the data collected at the next lowest pressure in a regression line. The SDBIndex is estimated from this data collection. In a next step, $\Delta$SDBIndex is calculated as the difference between SDBIndex at this next lowest pressure and SDBIndex at $P_{min}$. These steps are repeated sequentially for points at decreasing pressures to calculate the regression line and $\Delta$SDB$_{Min}$. In a next step, it is determined if $P_{MNT}$ is sufficiently close to SDBIndex$_{Min}$. That is, if $\Delta$SDBIndex is less than a threshold value, where the threshold value may be one of a constant and variable depending on the value of SDBIndex$_{Min}$ with respect to the therapeutic target. For example, if SDBIndex$_{Min}$ is less than 10, one could set the threshold for $\Delta$SDB to less than 5. That is, this process determines a compromise of a lower pressure that may be accepted for minimal increases in SDB that are nevertheless below the therapeutic target. This allows the optimal therapeutic pressure to the lowest pressure possible without significantly increasing the SDB of the patient. This results in the most comfortable pressure setting possible for the patient. In an embodiment, if SDBIndex$_{Min}$ is greater than 10 and up to 20, one could set the threshold for $\Delta$SDB to less than 2. That is, if the SDB is high, the choice of optimal pressure would be lowered only if accompanied by minimal changes in SDBIndex. If SDBIndex$_{Min}$ is greater than 20, one could set the threshold for $\Delta$SDB less than 1, indicating that the choice of optimal pressure would only be lowered if there was essentially no penalty in SDB. FIG. 13 depicts a value of $P_{MNT}$ inferred at a pressure below $P_{Min}$ at a point after which SDBIndex does not improve significantly upon pressure increase.

Figure 14:
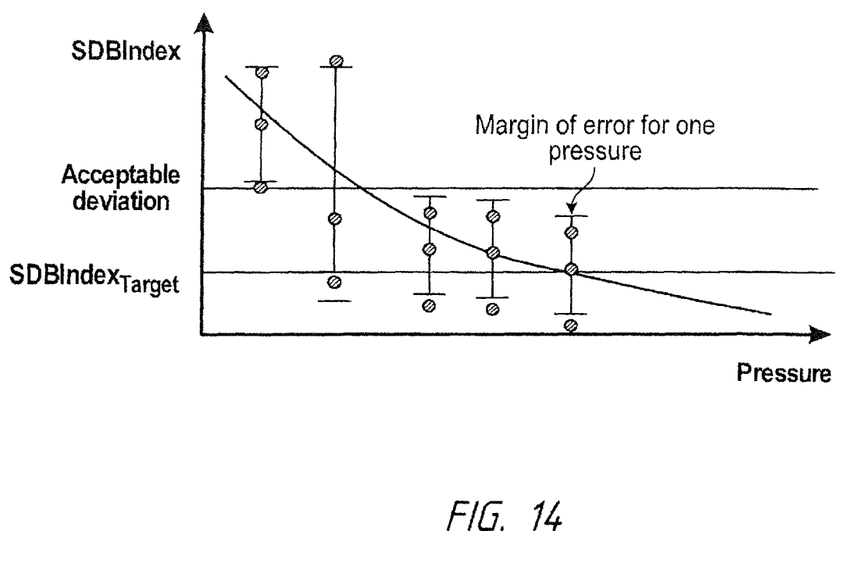
FIG. 14 depicts a calculation of a margin of error at each supplied pressure.

Once the data analysis of step 503 has been completed and a first optimal pressure has been chosen, the method proceeds to step 505 where the acceptability and confidence level of this result may be calculated. The verification step according to the disclosure is particularly useful in that many patients with SDB show variability of SDB indices at a single lower pressure, the variability diminishing at higher pressures. One may then, for example, choose the lowest pressure at or above the previous "optimal $P_{MNT}$" that has a margin of error still below the therapeutic threshold for the SDBIndex. Examples of statistics that capture the margin of error include: (a) one or two standard deviations of the SDBIndex at the proposed $P_{MNT}$ pressure related to (or exceeding) the therapeutic threshold for that SDBIndex; (b) the number, or percentage, of points at the proposed $P_{MNT}$ that have an SDBIndex below the therapeutic threshold (e.g., whether at $P_{MNT}$ more than 4-6 data points lie below OI=10); and (c) the magnitude by which the largest value of SDBIndex at the proposed $P_{MNT}$ deviates (exceeds) from the therapeutic threshold (e.g.; if the "worst" OI seen at the proposed $P_{MNT}$ is >20). FIG. 14 depicts a calculation of the margin of error at each pressure. The verification step 505 is also useful in that the "best" pressure from a sampled pressure range may still be clinically unacceptable, thus evidencing the need for further verification. In either of the above situations, further refinement of the $P_{MNT}$ may be required if the verification step 505 indicates that the chosen $P_{MNT}$ is not acceptable. In this case, either additional MNT data must be collected to lower or raise the $P_{MNT}$ or an alert may be generated for the clinician to intervene. The alert may include any of a visual display, audible alarm, etc.

After the $P_{MNT}$ has been found, the method proceeds to validation step 507 where the CPAP device is locked at the pressure PUNT for a predetermined evaluation period, such as, for example, several nights or weeks. During this period SDB Indices are monitored at the chosen pressure $P_{MNT}$ only. A fractional expression of nights meeting a failure criterion (e.g., wherein SDB per night>a therapeutic value, for example OI>15) is then calculated. If this fraction rises above a threshold, the multi-night slow titration may be reengaged. This step is performed to guarantee that the patient has not been incorrectly titrated and to monitor changes in pressure requirements over time. For patients with known significant night-to-night variability in CPAP pressure requirement that is felt to be acceptable, this last step could be disabled by the clinician, or the device could automatically switch to another mode of therapy than fixed CPAP (e.g., autotitration).

There are many modifications of the present disclosure which will be apparent to those skilled in the art without departing from the teaching of the present disclosure. For example, a combination of long windows with moderately abnormal SDB index and short windows with very abnormal SDB index can be used concurrently with the process to "abort and rescue" from data collection at a pressure that is clearly too low. The embodiments disclosed herein are for illustrative purposes only and are not intended to describe the bounds of the present disclosure which is to be limited only by the scope of the claims appended hereto.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art. It will further be appreciated that the data and/or components described above may be stored on a computer-readable medium and loaded into memory of the computing device using a drive mechanism associated with a computer readable storing the computer executable components such as a CD-ROM, DVD-ROM, memory stick, or network interface. Further, the component and/or data can be included in a single device or distributed in any manner. Accordingly, general purpose computing devices may be configured to implement the processes, algorithms and methodology of the present disclosure with the processing and/or execution of the various data and/or components described above.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A continuous positive airway pressure (CPAP) device comprising:
    an air pressure supply arrangement configured to deliver a flow of pressurized air to an airway of a patient;
    a sensor configured to detect breathing patterns of the patient and generate breathing data; and
    a processor and a computer-readable medium including a set of instructions executable by the processor, the set of instructions operable to:
        direct the air pressure supply arrangement to deliver the flow at a first initial therapeutic pressure determined by a fast titration process analyzing breathing data corresponding to breathing patterns detected by the sensor during a first time window,
        direct the air pressure supply arrangement to adjust the flow to a first modified therapeutic pressure determined by a slow titration process based on the first initial therapeutic pressure, until a sleep disorder index is greater than a predetermined threshold, wherein the sleep disorder index corresponds to at least one of a frequency or severity of sleep disordered breathing detected by the sensor during a preceding time interval,
        direct the air pressure supply arrangement to adjust the flow to a second initial therapeutic pressure determined by the fast titration process analyzing breathing data corresponding to breathing patterns detected by the sensor during a second time window, and
        direct the air pressure supply arrangement to adjust the flow to a second modified therapeutic pressure, the second modified therapeutic pressure determined by the slow titration process based on the second initial therapeutic pressure and the sleep disorder index.

2. The device of claim 1, wherein the fast titration process determines the first initial therapeutic pressure based on sleep disordered breathing detected by the sensor during the first time window.

3. The device of claim 1, wherein the slow titration process adjusts the first modified therapeutic pressure independent of the sleep disorder index.

4. The device of claim 3, wherein the slow titration process adjusts the first modified therapeutic pressure based on a range of pressures from a first value below the first initial therapeutic pressure to a second value above the first initial therapeutic pressure.

5. The device of claim 1, wherein the first modified therapeutic pressure and the second modified therapeutic pressure are determined by the slow titration process so as to reduce at least one of severity or frequency of sleep disordered breathing detected by the sensor.

6. The device of claim 1, wherein the first time window is a single therapeutic session.

7. The device of claim 1, wherein the first time window extends across a plurality of therapeutic sessions.

8. The device of claim 1, wherein the slow titration process recursively adjusts the first modified therapeutic pressure across a plurality of therapeutic sessions until the sleep disorder index is greater than the predetermined threshold.

9. The device of claim 1, wherein the slow titration process determines the first modified therapeutic pressure based on sleep disordered breathing detected by the sensor during the preceding time interval.

10. The device of claim 9, wherein the first modified therapeutic pressure is an estimate of an optimal therapeutic pressure.

11. A method of controlling a continuous positive airway pressure (CPAP) device, the method comprising:
(i) setting the CPAP device to deliver a flow of pressurized air to an airway of a patient at a first initial therapeutic pressure, the first initial therapeutic pressure determined by a fast titration process analyzing breathing data corresponding to breathing patterns of the patient during a first time window;
(ii) adjusting the flow to a first modified therapeutic pressure, the first modified therapeutic pressure determined by a slow titration process based on the first initial therapeutic pressure;
(iii) repeating step (ii) until a sleep disorder index is greater than a predetermined threshold, wherein the sleep disorder index corresponds to at least one of a frequency or severity of sleep disordered breathing of the patient during a preceding time interval;
(iv) adjusting the flow to a second initial therapeutic pressure, the second initial therapeutic pressure determined by the fast titration process analyzing breathing data corresponding to breathing patterns of the patient during a second time window; and
(v) adjusting the flow to a second modified therapeutic pressure, the second modified therapeutic pressure determined by the slow titration process based on the second initial therapeutic pressure.

12. The method of claim 11, wherein the fast titration process determines the first initial therapeutic pressure based on sleep disordered breathing of the patient during the first time window.

13. The method of claim 11, wherein the slow titration process adjusts the first modified therapeutic pressure independent of the sleep disorder index.

14. The method of claim 13, wherein the slow titration process adjusts the first modified therapeutic pressure based on a range of pressures from a first value below the first initial therapeutic pressure to a second value above the first initial therapeutic pressure.

15. The method of claim 11, wherein the first modified therapeutic pressure and the second modified therapeutic pressure are determined by the slow titration process so as to reduce at least one of severity or frequency of sleep disordered breathing of the patient.

16. The method of claim 11, wherein the first time window is a single therapeutic session.

17. The method of claim 11, wherein the first time window extends across a plurality of therapeutic sessions.

18. The method of claim 11, wherein steps (ii) and (iii) are repeated across a plurality of therapeutic sessions.

19. The method of claim 11, wherein the slow titration process in step (ii) determines the first modified therapeutic pressure based on sleep disordered breathing of the patient during the preceding time interval.

20. The method of claim 19, wherein the first modified therapeutic pressure is an estimate of an optimal therapeutic pressure.

* * * * *